(12) United States Patent
Melnyk et al.

(10) Patent No.: US 6,276,933 B1
(45) Date of Patent: Aug. 21, 2001

(54) DENTAL TRANSLUCENCY ANALYZER AND METHOD

(76) Inventors: Ivan Melnyk, 604 Cottonwood Ave, Coquitlam (CA), V3J 2S4; Andrew H. Rawicz, 7216 Hewitt Str., Burnaby (CA), V5A 3M2; Pawel Kowalski, 459 Ailsa Ave., Port Moody (CA), V3H 1A2

( * ) Notice: Subject to any disclaimer, the term of this patent is extended or adjusted under 35 U.S.C. 154(b) by 0 days.

(21) Appl. No.: 09/531,517

(22) Filed: Mar. 21, 2000

(51) Int. Cl.[7] .............................. A61C 19/10; G10J 3/46
(52) U.S. Cl. .............................................. 433/26; 356/402
(58) Field of Search ............................... 433/26; 356/402, 356/404, 405, 407, 408

(56) References Cited

U.S. PATENT DOCUMENTS

| | | | |
|---|---|---|---|
| 4,468,197 | * | 8/1984 | Provost ................................. 433/29 |
| 4,836,206 | * | 6/1989 | Maxwell et al. ..................... 600/340 |
| 4,881,811 | * | 11/1989 | O'Brien ................................ 356/323 |
| 5,035,508 | * | 7/1991 | Carter et al. ........................ 356/416 |
| 5,387,977 | * | 2/1995 | Berg et al. ........................... 356/407 |
| 5,690,486 | * | 11/1997 | Zigelbaum ............................ 433/29 |
| 5,754,283 | * | 5/1998 | Keane et al. ........................... 356/73 |
| 5,766,006 | * | 6/1998 | Murljacic .............................. 433/26 |
| 5,851,113 | * | 12/1998 | Jung et al. ............................. 433/29 |
| 6,043,893 | * | 3/2000 | Treiman et al. ..................... 356/402 |
| 6,157,454 | * | 12/2000 | Wagner et al. ...................... 356/407 |
| 6,201,880 | * | 3/2001 | Elbaum et al. ........................ 433/29 |

* cited by examiner

*Primary Examiner*—John J. Wilson

(57) ABSTRACT

The invention relates to a dental device which measures the translucency of the anterior tooth that is adjacent to the tooth to be restored and gives the translucency factor that is used for the creation of a natural looking repaired tooth. The device illuminates the incisal part of the tooth with white light and detects the light from the opposite side of the tooth. Signals indicating the values of transmitted light, the calibrated light, and the ambient light are processed and displayed on the LCD as a translucency factor. The device comprises a handpiece with a U-shape distal holder. One part of the holder includes several illuminating fibers, whereas another part carries a corresponding number of detecting fibers. The device is applied to the tooth by touching the edge of the tooth with a bottom and one side of the holder which carries the detecting fibers.

8 Claims, 7 Drawing Sheets

DENTAL TRANSLUCENCY ANALYZER AND METHOD

BACKGROUND OF THE INVENTION

1. Field of the invention

The invention relates generally to esthetic dentistry, and more particularly, to the technical means that measure the translucency of dental materials and natural teeth in order to create naturally looked dental prostheses.

2. State of the Art

Translucency is a main factor that indicates the quality of the restorative dental procedures. A common situation frequently occurs when a patient gets a well color-matched restored anterior tooth, but it looks like a nonvital shade tab. This situation happens because the practitioner was not able to determine the translucency level in teeth that were adjacent to the damaged tooth and served as references for color matching. A translucency mismatch is most crucial for an incisal part of the anterior tooth which contributes mostly to the natural appearance of the patient's teeth.

A procedure for proper color matching is performed by the visual comparison of teeth against shade guide color standards. A significant problem with the visual method is that its success depends upon the color vision of the practitioner. Moreover, even in the case of perfect color vision, the dental color matching procedure can be quite anxiety provokingfor the practitioner because color and translucency change along the tooth. In order to be normalized, standard dental color shades are classified by considering the color only in the central part of the shade tab. The variation of translucency is not included in the shade description because it will affect the visual perception of the teeth and shade tabs. As a result, for matching the incisal translucent part, the practitioner must guess which central part of the nontranslucent shade tabs looks closer to the natural translucent tooth.

The recent prior art aimed to overcome the problem associated with the visual analysis of dental translucency by applying fiber optics for illuminating the tooth and for detecting the light scattered from the same side of the tooth. The idea was to determine the translucency factor by separate illuminating of different areas of the tooth with a few light sources, as described in U.S. Pat. No. 5,798,839 or by detecting the light scattered at different distances from a single light source as described in U.S. Pat. No. 5,851,113. There is one major technical obstacle to successful clinical implementation of these techniques. It is explained below without being bound by theory.

A translucent object appears like a milky glass. The higher the translucency, the more transparent object seems. The translucency parameter may be defined as a difference between color parameters that were taken when the object was analyzed against two backings, one ideally white and another absolutely dark. Consider an absolute transparent object, such as optical glass, for instance, and use a Lab color system that is based on the use of L, a, b color parameters. If the glass is measured against the white backing, the color parameters will be $L_w=100$, $a_w=0$, and $b_w=0$ which corresponds to an ideal white standard placed under the glass (reflection from the glass is neglected). When the same glass is measured against an absolutely dark backing, all color parameters will be zero, $L_b=a_b=b_b=0$, because no light is transmitted at all. Therefore, the color difference will be $\Delta L=L_w-L_b=100$, $\Delta a=a_w-b_b=0$, and $\Delta b=b_w-b_b=0$, and thus, the transluce absolute transparent glass equals 100.

However, the foregoing prior arts are entirely based on measurement of the backscattered light. They will indicate zero signals for both types of glasses mentioned above no light is scattered back in the direction from where light came. In other words, the prior arts are not able to distinguish between transparency and darkness because absorption which is independent of scattering contributes equally to transmittance and reflection. In the case of teeth, nonsensitivity to absorption will increase the color difference due to the spectral dependence of light propagation into the enamel and dentin. As described elsewhere, different color components have different absorption and scattering parameters. This example shows that translucency of the teeth has to be measured in a direct mode, namely by measuring the light (flux $F_t$) that passed through the tooth and has continued in the same direction as the incoming light. If $F_O$ is the incoming flux, the translucency factor, TR, can be expressed as a ratio, $TR=F_t/F_O \times 100$.

Earlier prior art was connected to the direct measurement of tooth transmission as described in U.S. Pat. No. 4,881,811. The technique has employed an integrating sphere that touched the external surface of the tooth while the tooth was illuminated from the internal side using a flexible fiber optic. The sphere was mounted in a probe that was connected to a remote spectrophotometer. The main disadvantage of this prior art is that it measures the total transmittance of the tooth because it collects the light that is scattered at all possible angles, from 0 up to 90 degrees. Another disadvantages of this prior art was the complexity and enlarged size of the probe. These do not allow for measuring a portion of the tooth that is necessary for the restoration of natural looking teeth. In addition, this prior art is not portable because it requires a cable connection with the remote spectrophotometer.

Another prior art that can be implemented for the translucency measurement of teeth is the fiber optic transillumination (FOTI) technique used for detecting cavities. It is comprised of an illuminating fiber bundle that illuminates the tooth from a powerful polychromatic light source and receiving fiber bundle that transfers a projection of the tooth to a screen or videocamera. This prior art is very complex and non-portable as it requires a powerful light source, and cannot provide an accurate measurement of translucency because the projective image is formed mostly by light scattered from the entire body of the tooth, not from the portion of the tooth that must be analyzed.

It is, therefore, an object of the invention to provide a dental translucency analyzer that is small and portable. It is also an object of the invention to provide a dental translucency analyzer able to measure translucency in a small portion of teeth and dental materials.

SUMMARY OF THE INVENTION

The foregoing objects are achieved by this invention which provides a dental translucency analyzer and method for measuring translucency of teeth that are adjacent to the damaged tooth.

According to the present invention, a dental translucency analyzer measures translucency in a small portion of the tooth by employing an illuminating fiber optic which is positioned at the back side of the tooth and a receiving fiber optic which is positioned at the front side of the tooth. The number of illuminating and receiving fibers is the same. Both fiber optics comprise low aperture optical fibers that transmit light within a relatively narrow angle. The proximal ends of the illuminating fiber optic are coupled to white light emitting diodes (LED), while distal ends of the receiving fiber optic are coupled to photodetectors. The distal ends of the illuminating fiber optic and the proximal ends of the detecting fiber optic surround the tooth via a U-shape holder, each distal end of an illuminating fiber faces a corresponding proximal end of a receiving fiber. Such a pair comprises a measuring channel that transilluminates the tooth at a certain position and detects the light that passes through the tooth in the same direction with illuminating light. In order to provide measurements in different portions of the tooth, the fiber optics may consist of several fibers that are located in a row at different distances from the edge of the tooth.

The photodetectors are connected to an electronic unit that processes signals indicating the translucency of the tooth and displays the result on an LCD display. The electronic unit is comprised of a microcontroller, a converter, a power supply, and drivers.

All fiber optics, LEDs, photodetectors, LCD and electronic components may be mounted in one handpiece that can be easily manipulated and kept as a conventional practitioner's tool without using a cable connection. The practitioner touches the tooth with one side of the U-shaped holder, and the device will automatically give a value of translucency. Because of the portability of the device, it may be possible to measure translucency along the crown of the tooth.

An advantage of the present invention is that the dental translucency analyzer is small and portable and can be easy operated by one hand. Another advantage of the present invention is that translucency of the tooth is measured in a direct mode without affecting the results by uncertain absorption and scattering parameters of the tooth. Yet another advantage is that translucency of the tooth can be measured in a small area of the tooth or several small areas of the tooth, thus, providing the possibility of an exact color restoration for the repaired tooth.

DETAILED DESCRIPTION OF THE INVENTION

Figure 1:
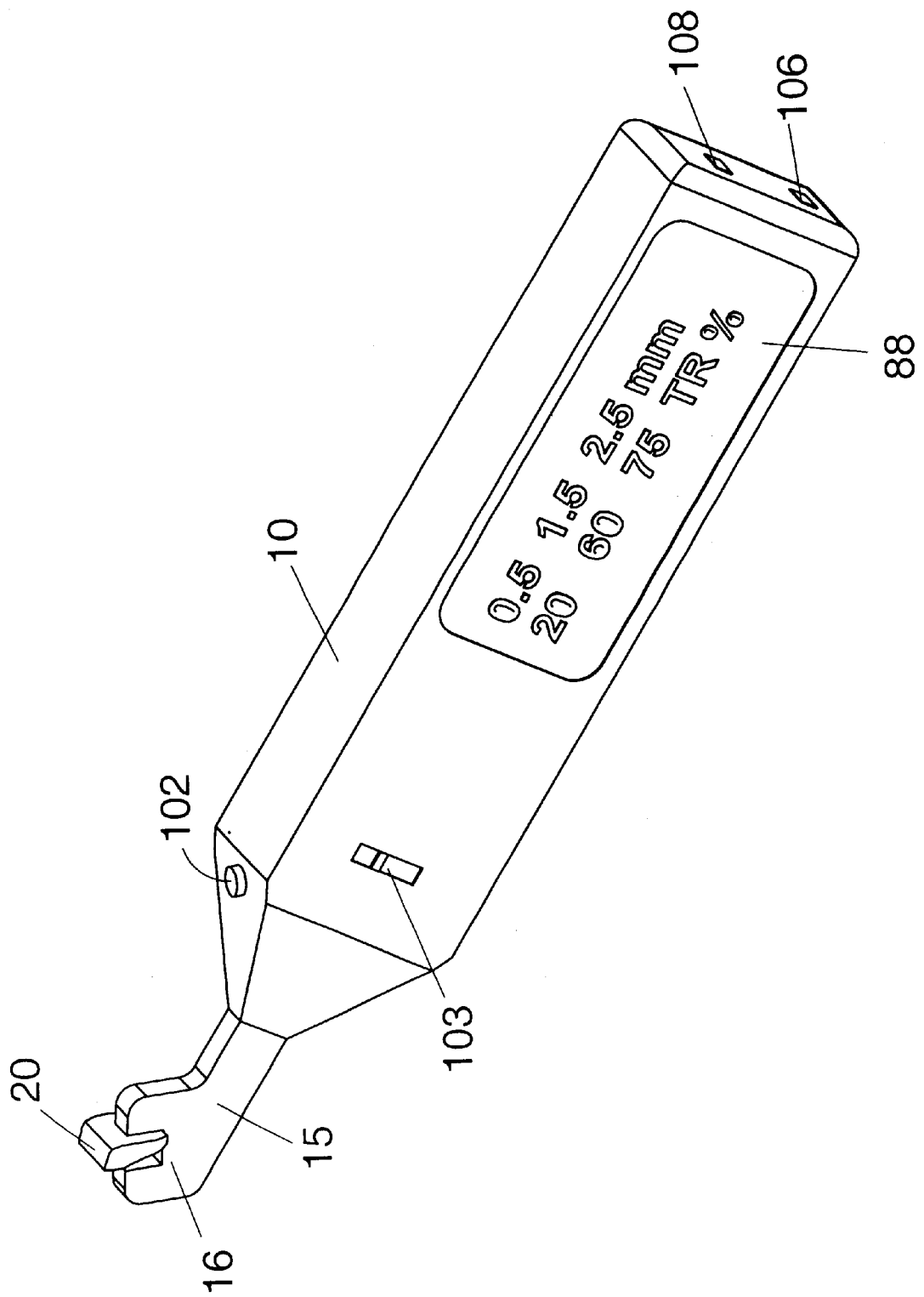
FIG. 1 is a general view of a preferred embodiment of the dental translucency analyzer in relation to a measured tooth.
Figures 2A, 2B:
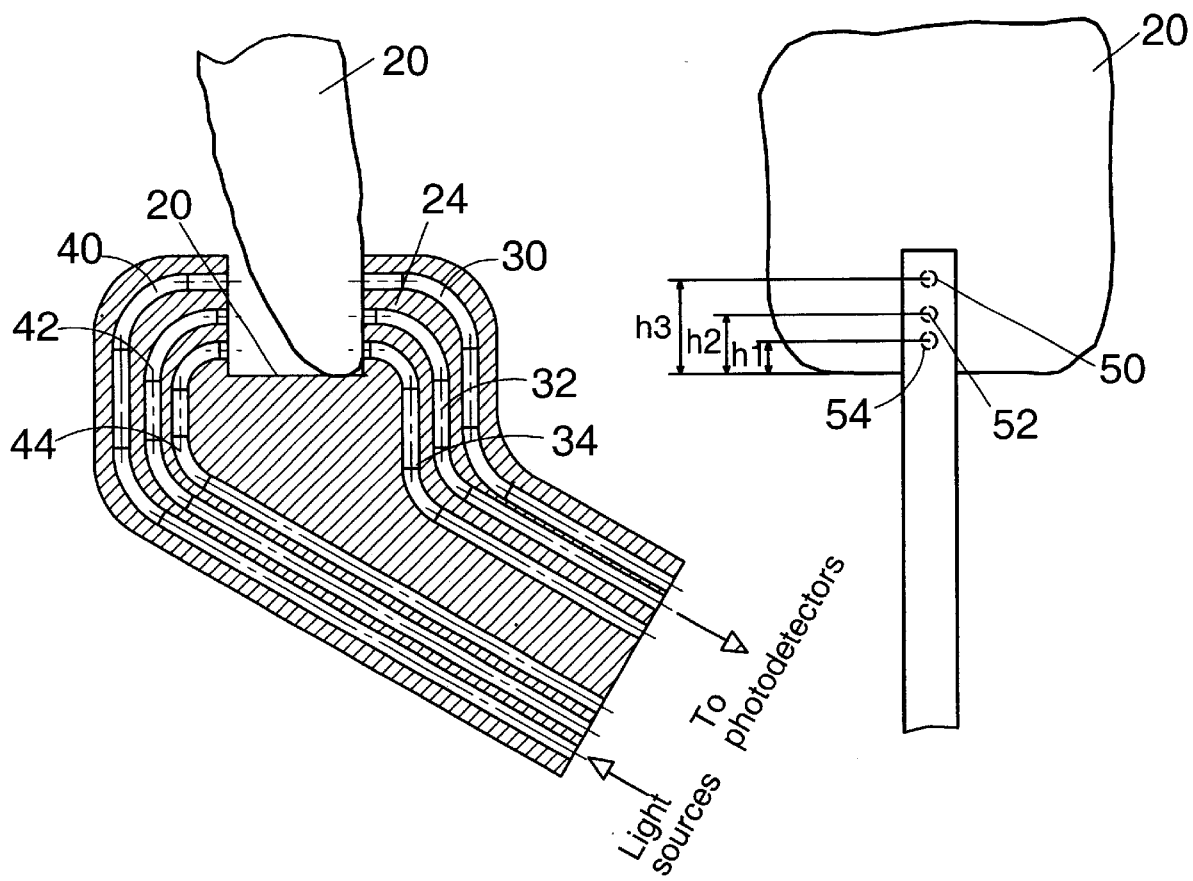
FIG. 2A is a detailed section view of a distal tip of the dental translucency analyzer of FIG. 1 and position of the distal tip in relation to the tooth.
FIG. 2B is a front view of the distal tip touching the tooth of FIG. 2A.

With reference to FIG. 1, the general design of a dental translucency analyzer according to the present invention shall be further explained. Essentially, the analyzer is designed as a handpiece that comprises a body (10) and a distal tip (15). The distal tip comprises a U-shaped holder (16) that is applied to a tooth (20) in such a way that the tooth is in contact with a bottom (22) and a right side (24) of the holder as shown in FIG. 2A. The right side of the holder carriers a plurality of receiving optical fibers (only three fibers (30), (32), and (34) are shown in FIG. 2A). A left side of the holder carriers a plurality of receiving optical fibers (only three fibers (40), (42), and (44) are shown in FIG. 2A). The distal end of each illuminating fiber faces the proximal end of the corresponding receiving fiber, and thus, the axes between the ends of the fibers create a plurality of measuring points (50), (52), and (54) as shown in FIG. 2B. The detecting fibers are coupled with a corresponding number of photodetectors, and the illuminating fibers are coupled with the corresponding number of light sources (both not shown in FIG. 2A).

Figure 3:
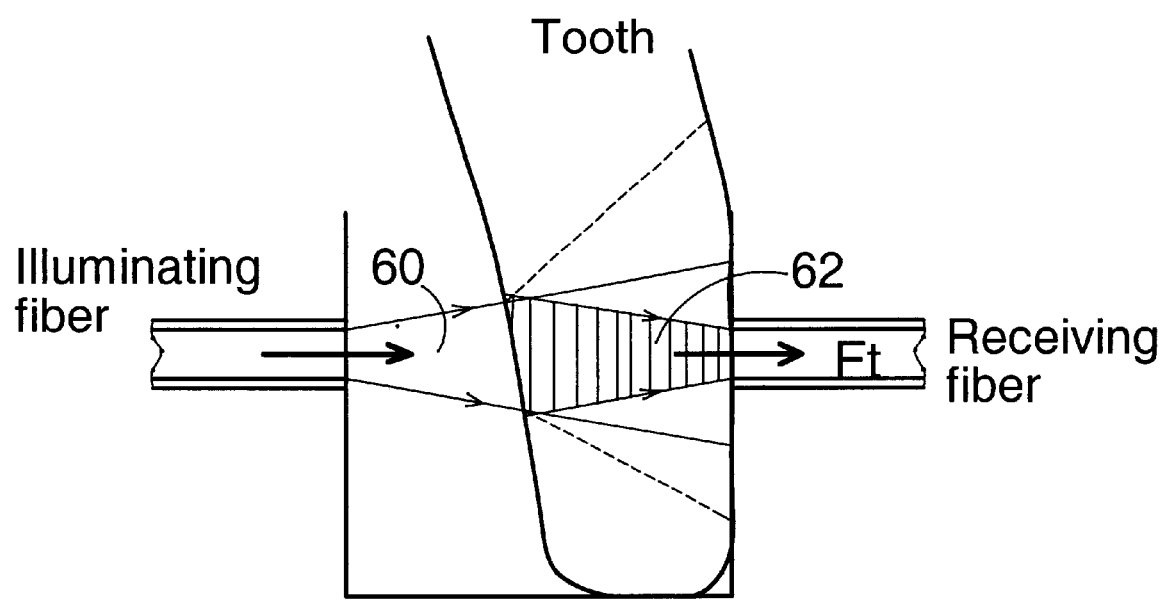
FIG. 3 is a schematic view of the illuminating and receiving fiber pair of FIG. 2A.

Both illuminating and receiving fibers are preferably low aperture optical fibers. An illuminating fiber irradiates the tooth within a narrow solid angle (60) as shown in FIG. 3. A corresponding receiving fiber detects light transmitted through the tooth (flux Ft) within a narrow solid angle (62). The fibers are located at various distances from the bottom of the holder with increments from 0.5 to 2.0 mm, preferably 1.0 mm.

Figure 4:
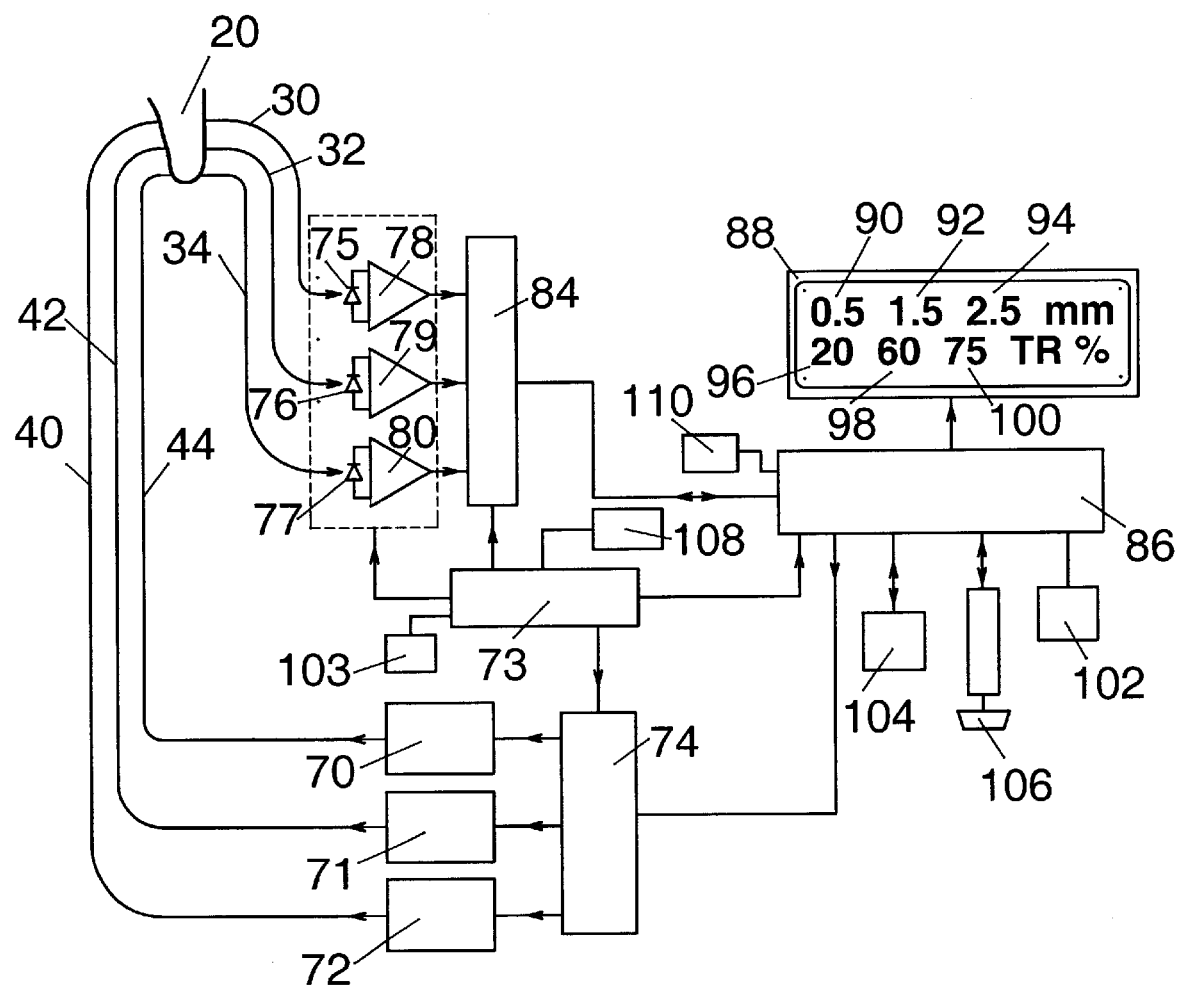
FIG. 4 is a schematic view of the electronic system of the dental translucency analyzer.

A schematic of the preferred embodiment of the electronic unit is shown in FIG. 4. The illuminating fibers (40), (42), and (44) are coupled to white polychromatic light sources (70), (71), and (72), respectively. The light sources are powered from a power supply (73) through a driver (74). Preferably, the light sources are white LEDs with operating voltages from 3 to 5 volts. The receiving fibers (30), (32), and (34) are connected to photodetectors (75), (76), and (77), respectively. The photodetectors are preferably silicone photodiodes. The photodetectors (75), (76), and (77) are connected to amplifiers (78), (79), and (80), respectively. The amplifiers are connected to an analogto-digital converter (84). The analog-to digital converter is connected to a microcontroller (86). The microcontroller indicates the results of the measurement on a liquid-crystal-display (LCD) (88). The indication results preferably include two lines of data, distances h1, h2, h3, ((90), (92), (94), accordingly), and the corresponding calculated data of translucency (96), (98), (100). The distances h1, h2, h3 are fixed for the design of the distal tip. In another embodiment, LCD may indicate "standby", "ready", "calibration" and other similar modes that make the device more user friendly.

The mode can be chosen by a switch (102) that is connected to the microcontroller (86). The switch can be located at any convenient place on the handpiece, preferably closer to the distal tip (15) as shown in FIG. 1. It can be activated by a finger or automatically when a proper contact of the holder (16) with the tooth (20) is achieved. In another embodiment, the LCD may show additional useful information such as the preferable composition of the restorative materials that gives the desired translucency. This data is processed in the microcontroller (86) by comparing the measured translucency with data stored in memory (104). The stored data may consist of values for translucency and standard recipes that combine a certain percentage of clear and opaque porcelains or plastics. A port (106) may be connected to the microcontroller. The port may be used for communication with dental image software, a patient database, communication with the dental lab performing the restoration, and other related purposes. A power switch (103) that connects the battery with the electronic circuit may be located at any convenient place on the handpiece, preferably on the front side of it as shown in FIG. 1. A connector (108) may be optional to the dental translucency analyzer if a rechargeable battery is used. Preferably, it is located in the bottom of the body as shown in FIG. 1. A speaker (110) can be connected to the microcontroller signaling the powering, calibration, and measurement.

Figure 5:
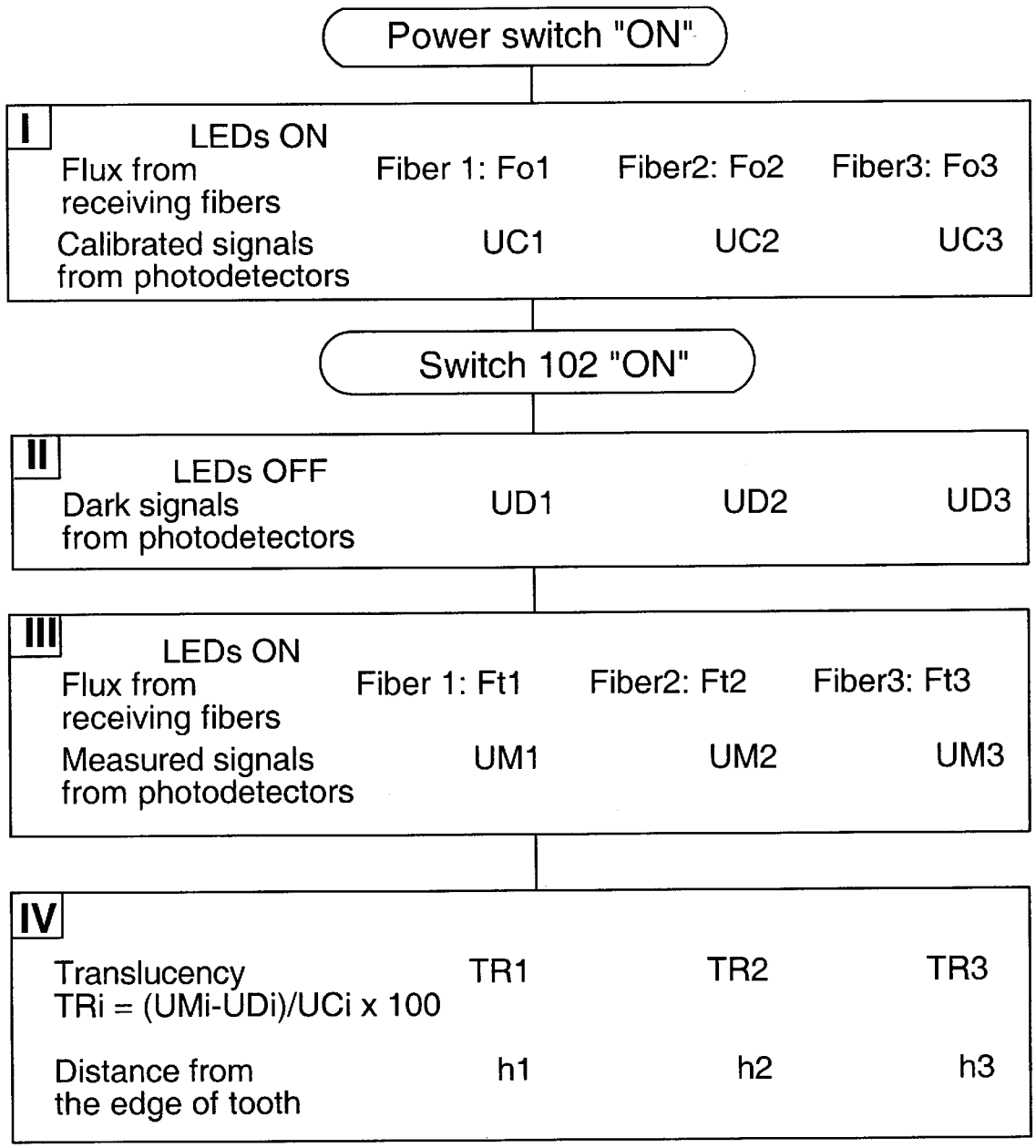
FIG. 5 is a flow chart of the operation of the dental translucency analyzer.
Figure 6:
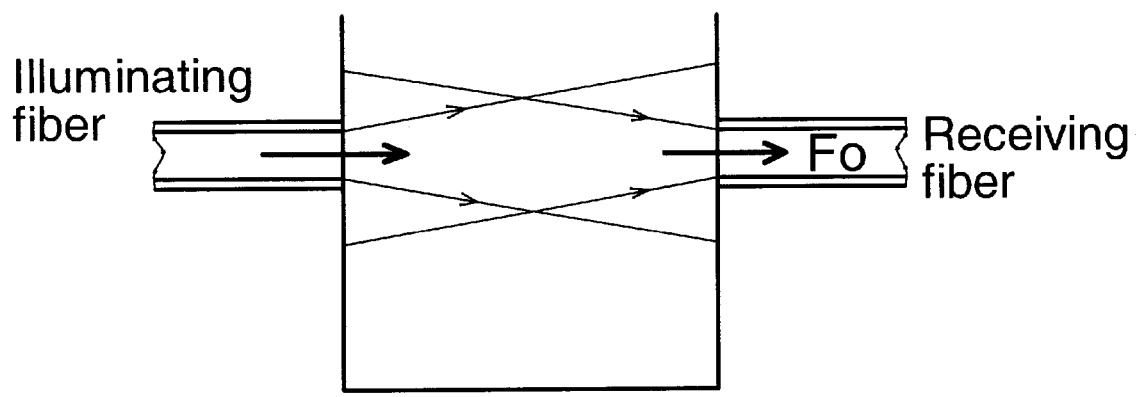
FIG. 6 is a schematic view the receiving and illuminating fiber pair during the calibration of the dental translucency analyzer.

With reference to FIG. 1, FIG. 5 and FIG. 6, the action of the dental translucency analyzer shall further be explained. Immediately after turning on the power switch (103), while still not applying the distal tip (15) to the tooth (20), a step I (calibration, or measurement of incoming fluxes Fo) is performed. Each LED is powered one by one in a sequence mode by a normalized pulsed current. Each receiving fiber gets its incoming flux Fo shown in FIG. 6 that comes from the corresponding illuminating fiber after passing the distance between the left and the right sides of the U-shape holder (fluxes Fo1, Fo2, and Fo3 shown in FIG. 5 for three fibers design mentioned above). The fluxes Fo are not necessary the same in each channel as they depend of the LED-to-fiber coupling, the fiber transmission, the quality of fiber tips, the photodetector-to-fiber coupling, and other factors. Therefore, the calibration is necessary for providing an accurate and repeatable measurement. According with the present invention, the calibration is performed by measuring the fluxes Fo passed through the air space. Thus, the air space serves as a translucency standard (reasonably, the translucency of air can be accepted as 100%). The flux Fo is converted by the corresponding photodetector to a calibrated signal UC (signals UC1, UC2, UC3, respectively). The values of these signals are stored in the microcontroller. When these measurements are done, all LEDs are turned off. In order to avoid illumination coming straight from surrounding light sources, the distal tip can be placed in a dark enclosure during calibration. After applying the distal tip (15) to the tooth (20) and activating the switch (102) the next steps are performed.

Step II (dark signals registration). The microcontroller registers dark signals UD (signals UD1, UD2, UD3 shown in FIG. 5). These signals are generated by the photodetectors mainly because of ambient illumination.

Step III (measurement of transmitted fluxes Ft). The LEDs are powered in the same way as was done in step I. Each receiving fiber receives flux Ft which transmits through the tooth at a certain distance h from the tooth's edge. The microcontroller registers a set of the signals UM (signal UM1, UM2, UM3 in FIG. 5) from the photodetectors.

Step IV (calculation of translucency). The translucency parameter, TR, is calculated by the microcontroller from the stored data for each distance h as $$TR=(UM-UD)/UC \times 100$$

and is expressed a percentage for convenience.

The calculated value TR is then displayed on the LCD, preferably as rows of h and TR as shown in FIG. 1. It can be used for preparing the recipes for the dental lab which is going to make the dental prostheses.

Figure 7:
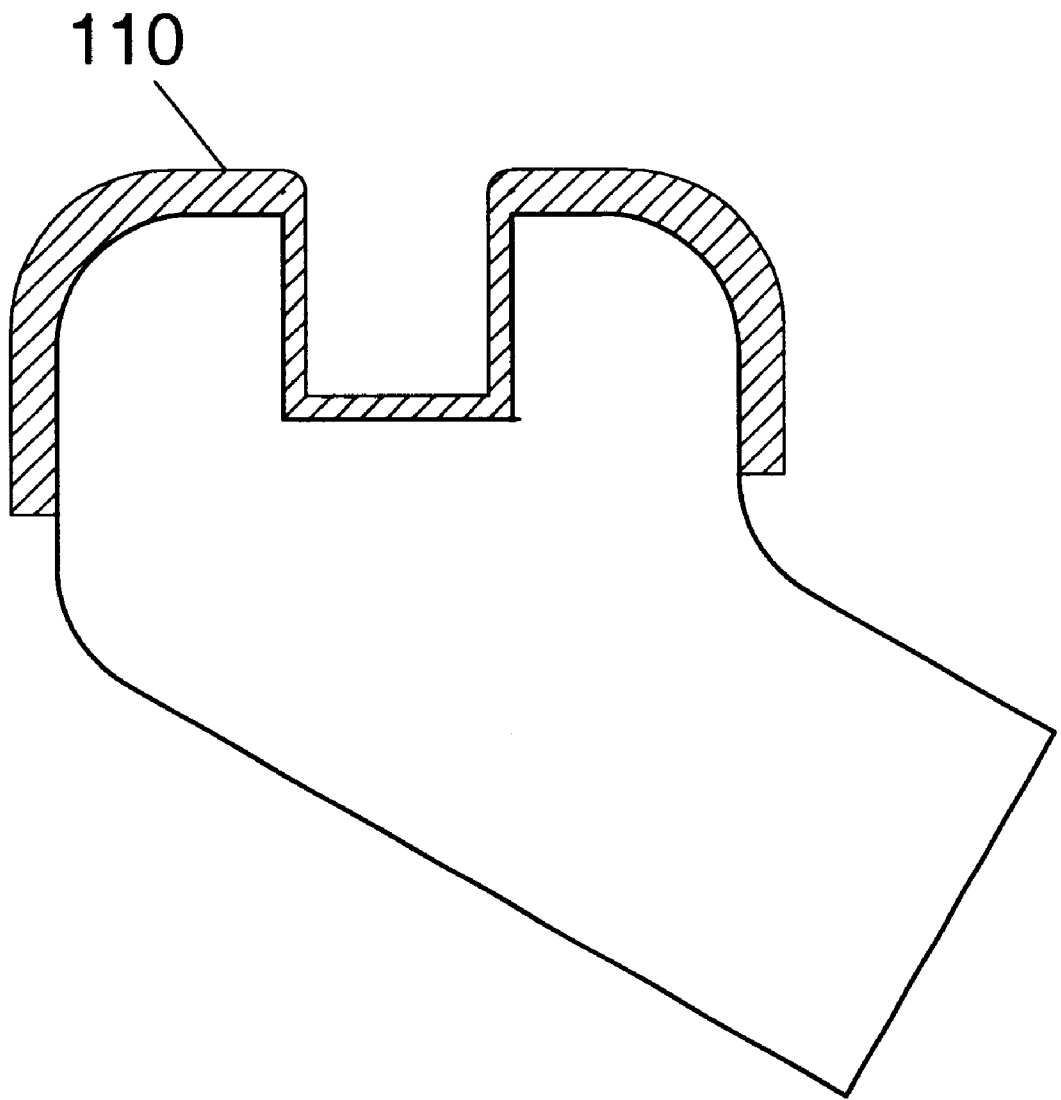
FIG. 7 is a view of the distal tip of the dental translucency analyzer with a disposable protective shield.

The distal tip (15) can be made disposable by pulling it from the body (10). In another embodiment, a thin disposable protective shield (112) can be applied to the distal tip as shown in FIG. 7. This shield will protect the patient against direct contact with the dental translucency analyzer. The shield can be made of a transparent material, preferably polystyrene or polyethylene. The calibration procedure (step I in FIG. 5) is performed after applying the shield.

The diameter of the illuminating and receiving fibers can be from 0.05 to 1.0 mm, preferably from 0.1 to 0.2 mm. The diameter of the receiving fiber determines the size of the zone that is detected by the dental translucency analyzer. This zone is much smaller than the width of the translucent incisal part of the tooth which is typically from one to four millimeters.

It should be pointed out that a great number of possible designs of the dental translucency analyzer according is possible within the scope of the present invention. For, example, a few more rows of illuminating and receiving fibers could be placed into the distal tip with corresponding LEDs and photodetectors attached in the body. This placement will allow the provision of translucency measurement in a lateral direction, and thus, more accurate data could be obtained from multiple portions of the tooth. In addition, a row of microlenses could be associated with the distal ends of the illuminating fibers for providing more directional illumination of the tooth.

What is claimed is:

1. A dental translucency analyzer for measuring the translucency parameter of an anterior tooth, such dental translucency analyzer comprising:
    a) a body that is made as a handpiece with a distal tip, wherein:
        said tip has a U-shape holder on its end comprising a bottom and two sides;
    b) a plurality of channels that illuminate said holder and detect a light passed through said holder, each said channel works in a controlled manner and includes:
        a light source;
        an illuminating optical fiber that is illuminated by said light source from its proximal input end, a distal output end of said fiber is placed in one side of said holder;
        a receiving optical fiber collecting a light that passes through said holder; a proximal input end of said fiber is coaxial with said distal end of said illuminating fiber and is located in the opposite side of said holder;
        a photodetector that is coupled to a distal output end of said receiving fiber;
    d) means for processing signals from said photodetectors to calculate a translucency factor wherein said means for processing includes a plurality of amplifiers, an analog-to-digital converter, a microcontroller and an activating switch;
    e) a display for displaying a message indicative of said calculated translucency factor;
    f) means for powering components indicative thereof, wherein this means is placed inside of said body.

2. The dental translucency analyzer of claim 1, wherein said light sources are white light emitting diodes.

3. The dental translucency analyzer of claim 1, wherein said illuminating and receiving optical fibers are low aperture optical fibers.

4. The dental translucency analyzer of claim 1, wherein distal output ends of illuminating fibers and proximal input ends of receiving fibers of said channels are located in a plane perpendicular to a bottom of said U-shape holder.

5. The dental translucency analyzer of claim 1, wherein each said channel is controlled in the following manner:
    calibration of signals from said photodetector including:
        powering said dental translucency analyzer from said powering means while not yet touching said tooth with said distal tip;
        powering said light source with a pulsed current, registration of calibrated signals from said photodetectors and storage of said calibrated signals in said microcontroller;

detecting of dark signals including:
  touching said tooth with said distal tip;
  activation of said activating switch;
  registration of dark signals from said photodetectors and storage of said dark signals in said microcontroller;
detecting the measured signals after detection of said dark signals including:
  powering said light source with a pulsed current;
  registration of measured signals from said photodetectors and storage of said measured signal in said microcontroller;
calculation of a set of the translucency factors as differences between said measured signals and said dark signals normalized by said calibrated signals.

6. The dental translucency analyzer of claim 1, wherein display is a liquid crystal display, and it indicates a row of translucency factors measured from each said channel and a row of distances between the bottom of said U-shape holder and proximal input end of each said receiving fiber.

7. The dental translucency analyzer of claim 1, wherein said distal tip touches said tooth by said bottom of said U-shape holder and one side of said holder where proximal input ends of said receiving fibers are located.

8. A dental translucency analyzer according to claim 1, further comprising:
  a disposable transparent shield applying to said distal tip.

* * * * *